Dec. 12, 1961 G. J. VON ABRAMS Plant Pat. 2,110
ROSE PLANT
Filed Dec. 8, 1960
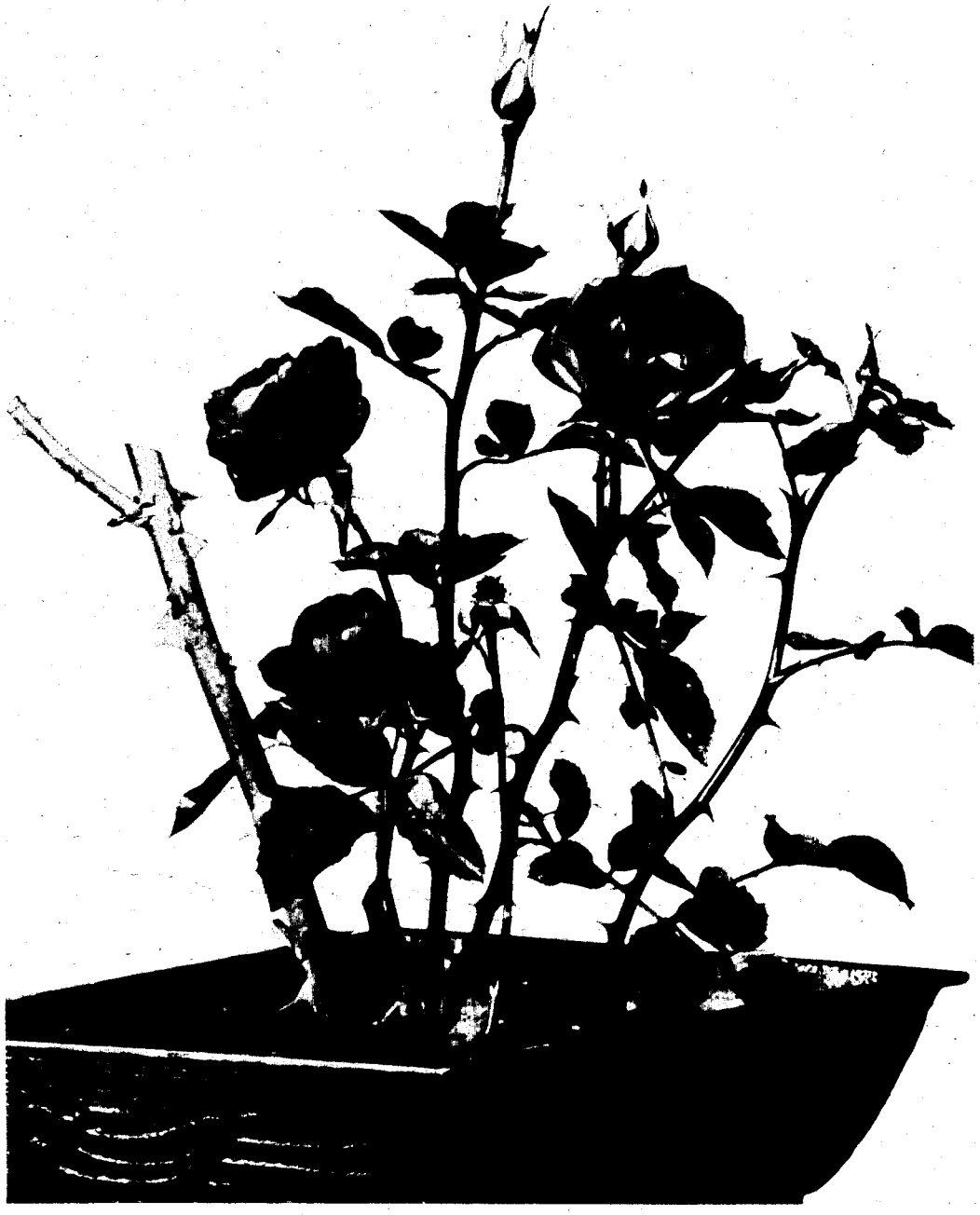
Inventor
Gordon J. Von Abrams
by L. R. Geisler, Atty.

United States Patent Office

Plant Pat. 2,110
Patented Dec. 12, 1961

2,110
ROSE PLANT

Gordon J. Von Abrams, Portland, Oreg., assignor to Eldon Pinkeney Dering, Scappoose, Oreg.

Filed Dec. 8, 1960, Ser. No. 74,747
1 Claim. (Cl. 47—61)

This invention comprises a new and distinct variety of rose plant of the commercial floribunda class which resulted from pollinating the rose variety "Improved Lafayette" (unpatented), with pollen of the variety "Carrousel" (Plant Patent No. 1,066). The objective of this breeding was, in part, to obtain a hardy, vigorous, large-growing floribunda bearing many dark red flowers. The principal distinguishing features of this new rose plant are the dull dark red color of the flower, with extreme darkening of the apex of the petal in senescence (sometimes to near black), the flat form of the flower with somewhat ruffled petals in a near-imbricated petal arrangement, and the unusual red coloration of the new growth and foliage.

This rose plant is taller-growing than most members of its class. It is intermediate in plant height between "Carrousel" and "Improved Lafayette," its flower color is darker duller red than either, and its flower form is fuller and more compact than either parent. Of rose varieties in commerce, it most nearly resembles the variety "Red Pinnochio" (Plant Patent No. 812). The flower form and general coloration of the two varieties are somewhat similar, but the new variety has more petals than Red Pinnochio, its flower color is darker duller red containing less blue, its bud form is less globular, its foliage is slightly more glossy, its foliage and new growth are more red in color.

This rose plant was propagated and grown by me and under my direction at Scappoose, Oregon. The crossing took place in the spring of 1953. The first flower was produced in the spring of 1954. The plant has been shown to hold its distinguishing characteristics through successive propagations by bud-grafting performed at Scappoose, Oregon. The general type of the plant is semi-hardy, medium tall bush, outdoor, seedling, for garden decoration.

The accompanying illustration shows the rose plant in color with separated blooms in different stages of development. There follows a more detailed description in which the following color references are used:

(1) Wilson, R. F.; Royal Horticultural Society Colour Chart, England, 1940.

(2) Ridgway, R.; Color Standards and Color Nomenclature, Washington, D.C., 1912.

(3) Nickerson Color Fan, Munsell Color Co., Baltimore, 1957.

*Flowers*

The flowers are borne from several to many per stem, in slightly irregular cluster. The main stem is long and strong, pedicel medium-long and stiff.

The plant blooms abundantly outdoors and blooms almost continuously outdoors during the growing season. The flowers have a slight fragrance.

Longevity: On plant outdoors in September, 9 days; cut flowers from outdoor plant, 7 days at room temperature in September. The flower opens well, but may be retarded by cold wet weather.

Size of full open flower: Medium (i.e., 7 cm.).

Petalage: Double (i.e., 45 petals).

Form: Full cupped or "compact" at first, becoming fairly flat, near-imbricated, petals appear ruffled.

*Flower color*

The following description of a newly-opened flower was made in September 1959, from a specimen, or specimens, grown outdoors near Scappoose, Oregon.

Outside petal: Outer surface—basal fan near white. General color near Chrysanthemum Crimson (Wilson, 824/2, page 169). Lighter tint of same hue toward base. Sometimes irregularly flushed with darker shades, to near black. Inner surface—basal fan small; near white. No close match in Wilson, Ridgway or Nickerson. Near between Cardinal Red (Wilson, 822/1, page 168) and Chrysanthemum Crimson (Wilson, 824%1, page 169) but more black, and with luminescent appearance. Lighter tint near base.

Intermediate petal: As outside petal, but very slightly lighter tints of same color.

Inside petal: As intermediate petal.

General color effect (face on): No good match. Near between Cardinal Red (Wilson, 822/2, page 168) and Chrysanthemum Crimson (Wilson, 824/2, page 169) but more black, with luminescent appearance.

The following description of a mature flower was made in September 1959, from a specimen, or specimens which had been opened for a period of three days on a plant grown outdoors, near Scappoose, Oregon.

Outside petal: Outer surface—basal fan small; near white. General color near between Rose Red (Wilson, 724, page 158) and Chrysanthemum Crimson (Wilson, 824/3, page 169) sometimes with darker shades near apex. Inner surface—basal fan near white. General color resembles Chrysanthemum Crimson (Wilson, 824, page 169) but appears darker, velvety, luminous. Slightly lighter tints of same hue near base. Frequently darker near apical margin, near Pansy Purple (Wilson, 928, page 177) to Purple Madder, (Wilson, 1028, page 181).

Intermediate petal: As outside petal, but less apical darkening.

Inside petal: As outside petal, but with less apical darkening.

General color effect (face on): No good match. Near Chrysanthemum Crimson (Wilson, 824, page 169), but a deeper shade and more luminous in appearance.

Behavior in senescence: Color becomes darker, more blue. In hot dry weather, the apical areas of the petals may become gradually dark purple, then brown. In extremely hot weather, the petals may become nearly black, appearing dessicated or burned. The petals tend to persist in either hot dry, or cool wet, weather.

*Further details of bud and flower*

Bud:

Pedicel—

*Size.*—Long (i.e., 6.5 cm.). Medium caliber (i.e. 2.5 mm.).

*Strength.*—Erect.

*Surface.*—Somewhat rough; several gland-tipped cilia; usually with none but sometimes with a few small reddish thorns.

*Color.*—Near Spinach Green (Ridgway, 29. GG–Y. *m*, Plate V), flushed (or entirely) near Maroon (Ridgway, 3. O–R. *m*, Plate I).

Sepals:

*Size.*—Medium small (i.e., 7 x 16 mm.)

*Form.*—Spear-shaped.

*Point.*—Nearly all with foliaceous terminal appendage, usually small (i.e., 2 x 8 mm.) with margins nearly entire.

*Lateral margins.*—With few gland-tipped cilia; most but not all with one, two or three small foliaceous appendages; rarely with one or few small bristles.

*Surface.*—Outer—quite smooth, glossy. Inner—tomentose.

*Color.*—Outer surface—near Scheeles Green (Wilson, 860/1 page 175) flushed near Victoria Lake (Ridgway, 1. RED. *k*, Plate I). Inner surface—near Mytho Green (Ridgway, 29'''. GG–Y. *b*, Plate XLI).

*Behavior.*—Reflex early; sometimes, but not always, recurve. Terminal foliaceous appendages sometimes grow to large size.

*Before calyx breaks.*—Size—medium small (i.e., 1.4 x 1.7 cm., excluding calyx tube and foliaceous appendages. Form—stubby pointed, with slight to inconspicuous "neck." With medium-small foliaceous appendages on surface of bud (on lateral margins of some sepals). With medium, slightly serrate, foliaceous parts extending beyond the tip of the bud one-third of the length of the bud or more. Color—near Scheeles Green (Ridgway, 33. GY–G. *i*, Plate VI) heavily flushed with near Burnt Lake (Ridgway, 71. V–RR. *m*, Plate XII).

*As calyx breaks.*—Color near Purple Madder (Wilson 1028, page 181).

*As first petal opens.*—Size—small (i.e., 2 x 2 cm.). Form—short, nearly square, with flat top. Color: outer surface—darker than Chrysanthemum Crimson (Wilson, 824, page 169), flushed near Violet Carmine (Ridgway, 69. RV–R. *m*, Plate XII) or darker; inner surface—darker, more luminescent than Cardinal Red (Wilson, 822, page 168).

Petals:

*Substance.*—Medium thick, medium hard; flexible.

*Texture.*—Outer surface—satiny. Inner surface—slightly velvety.

*Shape.*—Outside petal—the petals of the outermost row are usually small and somewhat contorted, cupped, with edges rolled; second row—broadly obovate (i.e., 3.5 x 3.5 cm.); apex slightly emarginate, with broad shallow notch. Intermediate petal: broadly obovate (i.e., 3.1 cm. wide x 3.4 cm. long); apex slightly emarginate, with broad shallow notch. Inside petal: obovate (i.e., 2.5 cm. wide x 3 cm. long); apex irregular; usually several petaloids.

*Plant*

Foliage: Leaves compound, usually 5 leaflets; abundant; medium size.

*Leaflet.*—Shape—ovate to near-oval; apex mucronate; base rounded to slightly acute; margins irregularly serate. Dimension: area—medium (i.e., 4 cm. wide x 6.5 cm. long); thickness—medium heavy. Surface—medium hard, smooth, glossy. Flexibility—slightly stiff, not brittle.

*Color.*—Mature: upper surface—near Parsley Green (Wilson, 00962, page 193), but bluer, darker; under surface—slightly darker than Light Elm Green (Ridgway, 27'. G–Y. *k*, Plate XVII) flushed near Hay's Maroon (Ridgway, 1'. RED. *m*, Plate XIII), particularly along veins. Immature: upper surface—near Diamine Brown (Ridgway, 3'. O–R. *m*, Plate XIII); under surface—near Vandyke Red (Ridgway, 1'. RED. *k*, Plate XIII).

*Rachis.*—Caliber—medium. Upper side—groove shallow, flat-bottom, slight pubescent; few to several gland-tipped cilia on lateral ridges. Under side—few gland-tipped cilia; very few thorns.

*Stipules.*—Size—medium large (i.e., 1.4 cm. long x 0.7 cm. wide, excluding the points). Margins—usually bristly, near laciniate, with bristles glandular. Points—long, slender, nearly straight; turn out at an angle near 45°.

*Disease resistance.*—Normally susceptible to "mildew" and "rust," as determined by field observation. No lab. tests.

Growth:

*Habit.*—Tall (for type) (3'–4') compact bush. Much branched.

*Vigor.*—Above average of class.

*Canes (in second year's growth).*—Medium caliber. Moderately corky.

*Main stems (of current year's growth).*—Color—near Light Elm Green (Ridgway, 27'. G–Y. *k*, Plate XVII); when polished, near Spinach Green (Ridgway, 29, GG–Y. *m*, Plate V). Surface—somewhat glaucous; few localized corky lesions. Thorns—medium large (i.e., 11 mm. long); base obovate, medium (i.e. 4 mm. wide x 11 mm. long); slightly hooked downward; color near Liver Brown (Ridgway, 7'. R–O. *m*, Plate XIV).

*Branches* (currently bearing senescent bloom).—Color—near Spinach Green (Ridgway, 29. GG–Y. *m*, Plate V) or darker; surface somewhat glaucous. Thorns: small (i.e., 3 mm.)—several to numerous; many gland-tipped; color near Vandike Red to red brown; large (i.e., 9 mm.)—numerous; hooked slightly downward; base obovate to near oval, medium (i.e., 3 x 9 mm.); color near Vandike Red (Ridgway, 1'. RED. *k*, Plate XIII); cilia—several to many, gland tipped; short; reddish.

*New shoots (in active growth).*—Color—near Victoria Lake (Ridgway, 1. RED. *m*, Plate I) or darker, variably flushed near Spinach Green (Ridgway, 29. GG–Y. *m*, Plate V). Thorns: large (i.e., to 8 mm)—numerous; hooked slightly downward base obovate to near elliptical; medium (i.e., 2 x 6 mm.); color near Vandike Red (Ridgway, 1'. RED. *k*, Plate XIII); small (i.e., to 3 mm.)—few to many; dark red; many gland-tipped; cilia—several; gland-tipped.

*Reproductive organs*

Stamens:

*Quantity.*—Moderate number.

*Position.*—Arranged about the pistils, on the outer edge of the disc of the calyx tube immediately inward from the petals.

*Filaments.*—Medium short (i.e. 5 mm.). Nearly all with anthers. Color pale yellow, near white.

*Anthers.*—Small (i.e., 1 x 2 mm.) Orange-yellow.

*Pollen.*—Sparse; visible. Dark yellow.

Pistils:

*Quantity.*—Moderate number.

*Styles.*—Free, but closely packed at base in cottony tissue. Long, various (i.e., 4 to 10 mm. above disc). Caliber ordinary; moderately contorted.

*Stigmas.*—Small, ordinary. Grayish yellow.

*Ovaries.*—Some exposed, most enclosed.

Receptacle and calyx tube:

*Size.*—Small (i.e., 9 mm. high x 8 mm. diameter).

*Shape.*—Near funnel-shape, slightly rounded.

*Disc.*—Narrow, not prominent. Slightly raised. Greenish-yellow.

*Surface.*—Smooth.

*Color.*—Near Scheeles Green (Wilson, 860/1, page 175) heavily flushed with, or entirely, near Victoria Lake (Ridgway, 1. RED. *k*, Plate I) or darker red.

Fruit aggregate ("seed pod"): Rarely develops beyond juvenile stages.

*Size.*—Small.

*Shape.*—Broadly obovate.

*Color.*—Medium orange to red-orange at maturity.

*Sepals.*—Seldom persistent.

Seeds: Medium number, small.

Having thus disclosed my invention, I claim:

A new and distinct variety of rose plant of the commercial "floribunda" class, substantially as herein shown and described, characterized particularly by the dull dark red color of the flower, showing extreme darkening of the apex of the petal in senescence, and by the unusually flat form of the flower, with somewhat ruffled petals in near-imbricated formation.

No references cited.